US008768461B2

(12) United States Patent
Stein

(10) Patent No.: US 8,768,461 B2
(45) Date of Patent: Jul. 1, 2014

(54) SYSTEMS AND METHODS FOR CONTROLLING PAIRED PACING INTERPULSE INTERVALS TO REDUCE CONTRACTILITY DISEQUILIBRIUM USING AN IMPLANTABLE MEDICAL DEVICE

(75) Inventor: Paul M. Stein, Oxnard, CA (US)

(73) Assignee: Pacesetter, Inc., Sylmar, CA (US)

( * ) Notice: Subject to any disclaimer, the term of this patent is extended or adjusted under 35 U.S.C. 154(b) by 115 days.

(21) Appl. No.: 13/226,277

(22) Filed: Sep. 6, 2011

(65) Prior Publication Data

US 2013/0060297 A1 Mar. 7, 2013

(51) Int. Cl.
*A61N 1/368* (2006.01)

(52) U.S. Cl.
USPC .......................................................... 607/9

(58) Field of Classification Search
CPC ............................ A61N 1/3627; A61N 1/368
USPC .......................................................... 607/9
See application file for complete search history.

(56) References Cited

U.S. PATENT DOCUMENTS

| 4,485,813 | A | 12/1984 | Anderson et al. |
| 4,535,774 | A | 8/1985 | Olson |
| 4,733,667 | A | 3/1988 | Olive et al. |
| 4,759,366 | A | 7/1988 | Callaghan |
| 4,884,576 | A | 12/1989 | Alt |
| 5,213,098 | A | 5/1993 | Bennett et al. |
| 5,800,467 | A | 9/1998 | Park et al. |
| 6,044,299 | A | 3/2000 | Nilsson |
| 6,208,900 | B1 | 3/2001 | Ecker et al. |
| 6,512,952 | B2 | 1/2003 | Stahmann et al. |
| 6,628,988 | B2 * | 9/2003 | Kramer et al. ............... 607/9 |
| 6,643,546 | B2 | 11/2003 | Mathis et al. |
| 6,666,826 | B2 | 12/2003 | Salo et al. |
| 6,738,667 | B2 * | 5/2004 | Deno et al. ............... 607/23 |
| 6,788,970 | B1 | 9/2004 | Park et al. |
| 7,142,916 | B2 | 11/2006 | Deno et al. |
| 7,184,833 | B2 | 2/2007 | Ganion et al. |
| 7,289,850 | B2 | 10/2007 | Burnes et al. |
| 7,437,192 | B2 | 10/2008 | Gill et al. |

(Continued)

FOREIGN PATENT DOCUMENTS

| EP | 1345651 B1 | 3/2006 |
| EP | 1347704 B1 | 12/2007 |

(Continued)

OTHER PUBLICATIONS

Rothe, Carl F. et al., "Cardiovascular Interactions: An Interactive Tutorial and Mathematical Model," Adv Physiol Edu. Jun. 2002;26(2):98-109.

*Primary Examiner* — Joseph Stoklosa

(57) ABSTRACT

Techniques are provided for use with implantable medical devices equipped to deliver paired postextrasystolic potentiation (PESP) pacing within a patient having an intact ventricle and a weakened ventricle. A first interpulse interval is determined for use with paired PESP pacing of the intact ventricle sufficient to achieve only relatively minimal potentiation within the intact ventricle. A second interpulse interval is determined for use with paired PESP pacing of the weakened ventricle sufficient to achieve relatively more significant potentiation within the weakened ventricle. Then, paired PESP pacing is delivered to the intact ventricle using the first interpulse interval while paired PESP is also delivered to the weakened ventricle using the second interpulse interval to reduce contractility disequilibrium within the heart caused by the weakened ventricle to achieve a matching of natural contractilities. In this manner, dual ventricular, independently timed, continuous PESP is provided.

18 Claims, 13 Drawing Sheets

(56) References Cited

U.S. PATENT DOCUMENTS

| | | |
|---|---|---|
| 7,599,739 B2 * | 10/2009 | Hudnall .................. 607/9 |
| 7,787,942 B2 | 8/2010 | Chinchoy et al. |
| 7,970,466 B2 | 6/2011 | Mulligan et al. |
| 2002/0058969 A1 | 5/2002 | Noren et al. |
| 2003/0055345 A1 | 3/2003 | Eigler et al. |
| 2003/0074029 A1 | 4/2003 | Deno et al. |
| 2004/0220640 A1 | 11/2004 | Burnes et al. |
| 2005/0075675 A1 | 4/2005 | Mulligan et al. |
| 2005/0090872 A1 | 4/2005 | Deno et al. |
| 2006/0149184 A1 | 7/2006 | Soykan et al. |
| 2006/0247692 A1 * | 11/2006 | Yang et al. .................. 607/9 |
| 2006/0247698 A1 * | 11/2006 | Burnes et al. ............... 607/9 |
| 2006/0247699 A1 | 11/2006 | Burnes et al. |
| 2007/0179390 A1 | 8/2007 | Schecter |
| 2007/0250122 A1 | 10/2007 | Warkentin et al. |
| 2008/0269825 A1 | 10/2008 | Chinchoy et al. |
| 2008/0306567 A1 | 12/2008 | Park et al. |
| 2010/0094371 A1 | 4/2010 | Bornzin et al. |
| 2010/0152804 A1 | 6/2010 | Kleckner et al. |
| 2010/0234906 A1 | 9/2010 | Koh |
| 2011/0022112 A1 | 1/2011 | Min |

FOREIGN PATENT DOCUMENTS

| | | |
|---|---|---|
| EP | 1686892 B1 | 11/2010 |
| WO | 0158518 A2 | 8/2001 |
| WO | 0158518 A3 | 1/2002 |
| WO | 0158518 A3 | 5/2002 |
| WO | 02053026 A2 | 7/2002 |
| WO | 02053026 A3 | 12/2002 |
| WO | 02053026 A3 | 7/2003 |
| WO | 2004096352 A1 | 11/2004 |
| WO | 2006115774 A2 | 11/2006 |
| WO | 2006115890 A2 | 11/2006 |
| WO | 2008134620 A1 | 11/2008 |
| WO | 2010135164 A1 | 11/2010 |

* cited by examiner

SYSTEMS AND METHODS FOR CONTROLLING PAIRED PACING INTERPULSE INTERVALS TO REDUCE CONTRACTILITY DISEQUILIBRIUM USING AN IMPLANTABLE MEDICAL DEVICE

FIELD OF THE INVENTION

The invention generally relates to implantable cardiac rhythm management devices such as pacemakers, implantable cardioverter-defibrillators (ICDs) and cardiac resynchronization therapy (CRT) devices and, in particular, to techniques for controlling paired pacing within patients having a weakened ventricle due to ischemia or heart failure.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

CRT is a form of therapy that seeks to normalize asynchronous cardiac electrical activation and the resultant asynchronous contractions within heart failure patients by delivering synchronized pacing stimulus to the ventricles. The pacing stimulus is typically synchronized so as to help to improve cardiac contractility and hence mitigate CHF. CRT and related therapies are discussed in, for example, U.S. Pat. No. 6,643,546 to Mathis et al., entitled "Multi-Electrode Apparatus and Method for Treatment Of Congestive Heart Failure"; U.S. Pat. No. 6,628,988 to Kramer et al., entitled "Apparatus and Method for Reversal Of Myocardial Remodeling With Electrical Stimulation"; and U.S. Pat. No. 6,512,952 to Stahmann et al., entitled "Method And Apparatus for Maintaining Synchronized Pacing." See, also, U.S. Patent Application No. 2008/0306567 of Park et al., entitled "System and Method for Improving CRT Response and Identifying Potential Non-Responders to CRT Therapy" and U.S. Patent Application No. 2007/0179390 of Schecter, entitled "Global Cardiac Performance."

Insofar as contractility is concerned, it is well known that due to its larger muscle mass and pressure development, the contractility of the left ventricle of the human heart is significantly higher than that of the right. Even with this disparity between right and left contractility, muscle wraps from the left ventricle enveloping the right ventricle provide a boost in effort to the right ventricle, thereby producing a functional equilibrium of cardiac output from the two ventricles. In some forms of CHF, the contractility of both ventricles fails, such as with idiopathic dilated cardiomyopathy. In other cases, one ventricle is independently depressed due to an ischemia that causes loss of musculature. In the latter case, a functional disequilibrium between the pumping of the ventricles develops, for example, when the left ventricular contractility becomes depressed toward the values of the right ventricle or even lower.

As noted, CRT may be used to mitigate CHF. Unfortunately, not all patients with CHF respond to CRT. In particular, patients without a wide QRS complex are not considered for CRT as these patients are deemed to be "non-responders." CRT therapy is deemed ineffective in these patients because the relatively narrow QRS may be indicative of a left-to-right contractility disequilibrium caused by the weakening of one of the ventricles and that disequilibrium remains even with proper CRT activation timing. Hence, it would be advantageous for the next generation of implantable medical devices to treat these CRT non-responders and other CRT non-candidates in an effort to restore the normal contractility state of the heart. In doing so, the entire heart muscle would approach its available peak efficiency.

One possible technique for extending CRT to nonresponders is to exploit post-extrasystolic potentiation (PESP). PESP is a physiological phenomenon whereby a premature cardiac activation will produce an ineffective beat but will then potentiate the mechanical activity of the subsequent beat. This potentiation is evidenced by increases in stroke volume, stroke work, systolic blood pressure and cardiac contractility. In brief, it is believed that the potentiation is due to an increase of calcium ions released into the sarcoplasmic reticulum that cause a greater cross-linking of actin and myosin filaments. The extrasystole also produces a compensatory pause that causes the subsequent beat to occur later than would be expected, slowing the heart rate.

Thus PESP may be used to enhance CRT by increasing contractility beyond what is typically achieved by merely restoring synchrony. Also, PESP may be used to slow the ventricles during atrial fibrillation (AF) because PESP tends to prolong the refractory interval. That is, the additional depolarization during a relative refractory period caused by the PESP pulse has the effect of extending the overall refractory interval. The longer refractory interval acts to block the conduction of rapid atrial impulses associated with AF. PESP thus can provide for rate control during AF. Further, PESP may be used to treat patients with low ejection fraction (EF) and narrow QRS heart failure, i.e. a form of heart failure where the electrical signals associated with ventricular depolarization (QRS complexes) are shorter than usual. PESP may also be used to treat cardiac insufficiency. Still further, PESP may be used to treat heart failure with preserved EF. Patients with heart failure with preserved EF can benefit because PESP enhances the rate of relaxation. PESP therapy and related techniques are discussed in: U.S. Pat. Nos. 7,184,833; 7,289,850; U.S. Patent Application 2007/0250122; U.S. Patent Application 2006/0149184; and U.S. Patent Application 2006/0247698.

FIG. 1 illustrates the effects of PESP. A first pair of traces illustrate a normal sinus rhythm (i.e. no PESP) by way of an electrocardiogram (ECG) 2 and a ventricular pressure graph 4. A first intrinsic depolarization 6 within the ECG causes the ventricles to contract, resulting in an increase in ventricular pressure 8. Each subsequent depolarization 6 triggers an increase in ventricular pressure 8 of about equal magnitude. In contrast, a second pair of traces 10 and 12 illustrate the effects of PESP. ECG 10 shows an initial depolarization 14 followed shortly thereafter by an extrasystolic pulse 16. The initial depolarization 14 triggers a contraction that causes an increase in ventricular pressure 18, as with normal sinus rhythm. The extrasystolic pulse 16 triggers an ineffective contraction that results a minimal increase in ventricular pressure 20. This is an ineffective beat that results in a compensatory pause before a next intrinsic depolarization, i.e. the next heartbeat is delayed. The ineffective beat also triggers PESP, which has the effect of potentiating the next beat. That is, the next intrinsic depolarization 22 triggers a stronger contraction that results in a much larger magnitude increase in ventricular pressure 24. This stronger contraction is due to the potentiation achieved via PESP. Note, though, that the potentiation achieved via PESP can degrade rapidly on subsequent beats due to the reuptake of extra calcium during the compensatory pause, resulting in less potentiation of subsequent beats.

To counter the degradation and maintain potentiation, continuous PESP techniques have been developed that exploit either coupled pacing or paired pacing. With coupled pacing, the implantable device senses a ventricular activation and paces at a particular coupling interval set to maintain potentiation at a consistent level. This is illustrated by way of traces 26 and 28 of FIG. 2. Each intrinsic depolarization 30 is followed by an extrasystolic pulse 32 (subject to a coupling interval), which triggers a potentiated contraction 34 with greater magnitude than unpotentiated contractions such as initial contraction 36. By continuously applying extrasystolic pulses subject to a suitable coupling interval, the resulting potentiation is maintained at more or less uniform levels. However, the lengthy compensatory pause following each extrasystolic pulse can result in a significant reduction in overall heart rate (sometimes reducing it by half), which may have the effect of reducing overall cardiac output and hence counteracting some or all of the benefits achieved by the potentiation. Hence, although coupled pacing can avoid the degradation of potentiation occurring with non-continuous PESP, the sharp reduction in heart rate is problematic, at least within some patients.

Paired pacing can be used to avoid degradation of potentiation while also avoiding the sharp drop in heart rate. Within FIG. 2, paired pacing is shown by way of traces 36 and 38. Pacing pulses are delivered at a rate high enough so that intrinsic depolarizations do not occur. The pacing pulses are delivered in pairs. A first pulse 40 of each pair triggers a corresponding contraction of the ventricles such as initial contraction 41. The second pulse 42 of each pair (delivered subject to an interpulse interval) then triggers PESP so as to potentiate subsequent contractions 44 to have a greater magnitude than unpotentiated contractions (e.g. initial contraction 41.) By continuously applying extrasystolic pulses subject to a suitable interpulse interval, the resulting potentiation is maintained at more or less uniform levels. Moreover, since the heart is paced to avoid intrinsic depolarization, the lengthy compensatory pause occurring with coupled pacing is avoided and hence elevated cardiac output can be maintained.

Paired and coupled pacing techniques are discussed in U.S. Published Patent Application No. 2010/0094371 of Bornzin et al., entitled "Systems and Methods for Paired/Coupled Pacing" and in U.S. patent application Ser. No. 11/929,719, also of Bornzin et al., filed Oct. 30, 2007, entitled "Systems and Methods for Paired/Coupled Pacing and Dynamic Overdrive/Underdrive Pacing." See, also, U.S. patent application Ser. No. 13/196,763, of Koh, filed Aug. 2, 2011, entitled "Systems and Methods for Controlling Paired Pacing based on Patient Activity for use with an Implantable Medical Device."

Despite the apparent advantages of continuous PESP—especially paired pacing—such techniques have sometimes met with resistance within the cardiac pacing community. One possible reason is that, as conventionally envisioned, paired pacing is applied only at a single site, such as a single site in the RV, or is applied by equal amounts in the LV and RV. As already noted, though, the contractility of one ventricle might be independently depressed due to loss of musculature because of an ischemic event. As such, a functional disequilibrium may develop between the weakened ventricle and the intact ventricle. Single-site PESP would do little or nothing to rebalance the two ventricles. Likewise, applying the same level of PESP to both the LV and RV where only one has been weakened would likely maintain the disequilibrium, and may even make it worse in some cases.

Accordingly, it would be desirable to provide improved techniques for controlling paired PESP that address these and other problems and it is to this end that aspects of the invention are generally directed. In particular, it is desirable to provide paired PESP techniques that would serve to rebalance RV and LV contractilities in cases where one ventricle is weakened and the other is intact. By successfully rebalancing the right and left contractilities, the entire heart muscle would approach its available peak efficiency. Moreover, a rebalancing of left and right contractility would allow CRT to be applied to at least some patients who are conventionally regarded as non-responders due to contractility disequilibrium.

SUMMARY

In an exemplary embodiment, a method is provided for use with an implantable cardiac stimulation device equipped to deliver paired PESP pacing within a patient having an intact ventricle and a ventricle weakened by an ischemic event. A first interpulse interval is determined for use with paired PESP pacing of the intact ventricle sufficient to achieve only relatively minimal potentiation within the intact ventricle. A second interpulse interval is determined for use with paired PESP pacing of the weakened ventricle sufficient to achieve relatively more significant—preferably maximum—potentiation within the weakened ventricle. Then paired PESP pacing is delivered to the intact ventricle using the first interpulse interval while paired PESP is also delivered to the weakened ventricle using the second interpulse interval to reduce contractility disequilibrium within the heart caused by the weakened ventricle to achieve a matching of natural contractilities. In this manner, dual ventricular, independently timed, continuous PESP is provided. The implanted device may be, for example, a pacemaker, ICD or CRT device.

Hence, aspects of the invention provide a system to separately extrasystole pace each ventricle using separate leads, one RV and one LV, to approach a matching of the natural contractilities. The goal is to maintain the contractility of the intact ventricle and potentiate the contractility of the weakened ventricle, the one with the muscular deficit caused, e.g. by a permanent ischemic event. To this end, one ventricle is paced with an interpulse interval that produces little or no potentiation and the other is paced with an interpulse interval that produces significant potentiation. It should be understood that both ventricles should be paced with an extrasystole, in this manner, to reduce the contractility disequilibrium.

That is, paired PESP should not be delivered only to the weakened ventricle but not the intact ventricle (as would be the case with single-site PESP.) Rather, paired PESP pacing should instead be delivered to both ventricles with the interpulse interval for the intact ventricle set to provide little or no potentiation.

In the case where there has been a large myocardial infarction due to a left anterior descending or left circumflex arterial occlusion, the RV functions normally, but the LV is weak. This results in a dilatation of the LV with mitral regurgitation and an increase in the left atrial pressure (LAP) with pulmonary congestion with the propensity towards pulmonary edema. To produce a better balance of contractility, the RV is preferably paced with a short interpulse interval, resulting in a relatively insignificant increase in the cardiac contractility in the RV, while the LV is paced with a much longer interpulse interval, resulting in a significant increase in the cardiac contractility in the LV. By independently increasing the output of the LV, the LAP and pulmonary congestion will then decrease. The risk of pulmonary edema would then likewise decrease. More importantly, in time, the heart would tend to remodel, with a decrease in dilatation and mitral regurgitation.

Conversely, for an example where the RV is weakened due to an ischemia but the LV is relatively intact, the LV interpulse interval is set substantially shorter than the RV interpulse interval to provide relatively minimal extrasystolic potentiation within the LV and maximum potentiation within the RV so as to significantly improve the contractility of the RV relative to the LV.

The appropriate intervals needed to achieve maximum potentiation within the weakened ventricle may be ascertained using echocardiographic or other hemodynamic assessment techniques or may be based on signals received from an implanted physiological sensor, such as a LV pressure sensor, RV pressure sensor or LAP sensor. Atrioventricular (AV/PV) and interventricular (VV) pacing intervals may also be adjusted by the device based on echocardiographic or other hemodynamic assessments or based on physiological sensor signals System and method implementations are described herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System and Method

Figure 1:
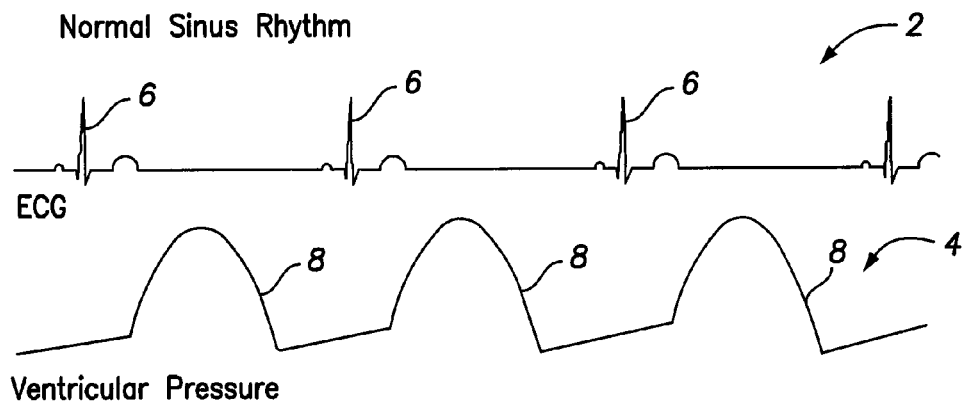
FIG. 1 is a graph illustrating non-continuous PESP techniques in accordance with the prior art.
Figure 1:
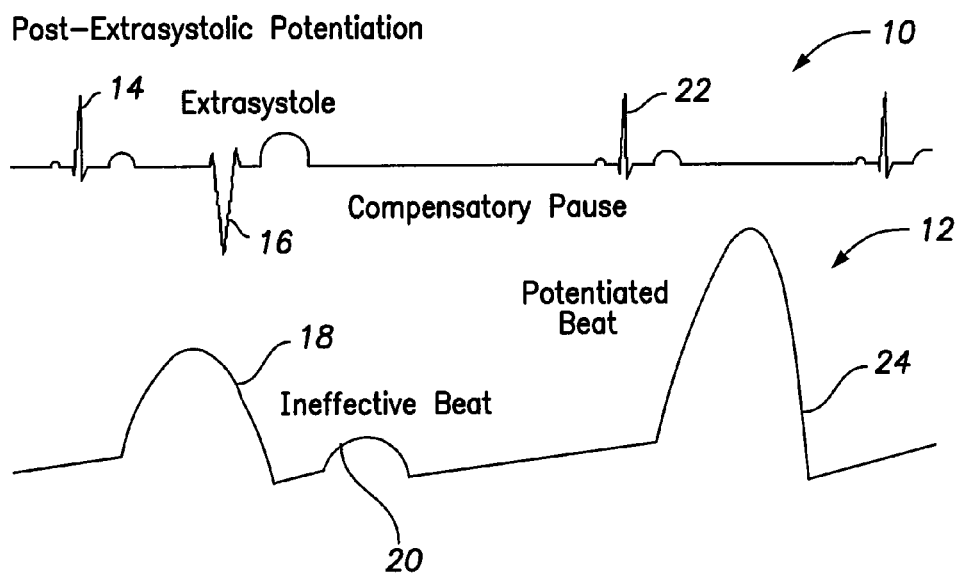
Figure 2:
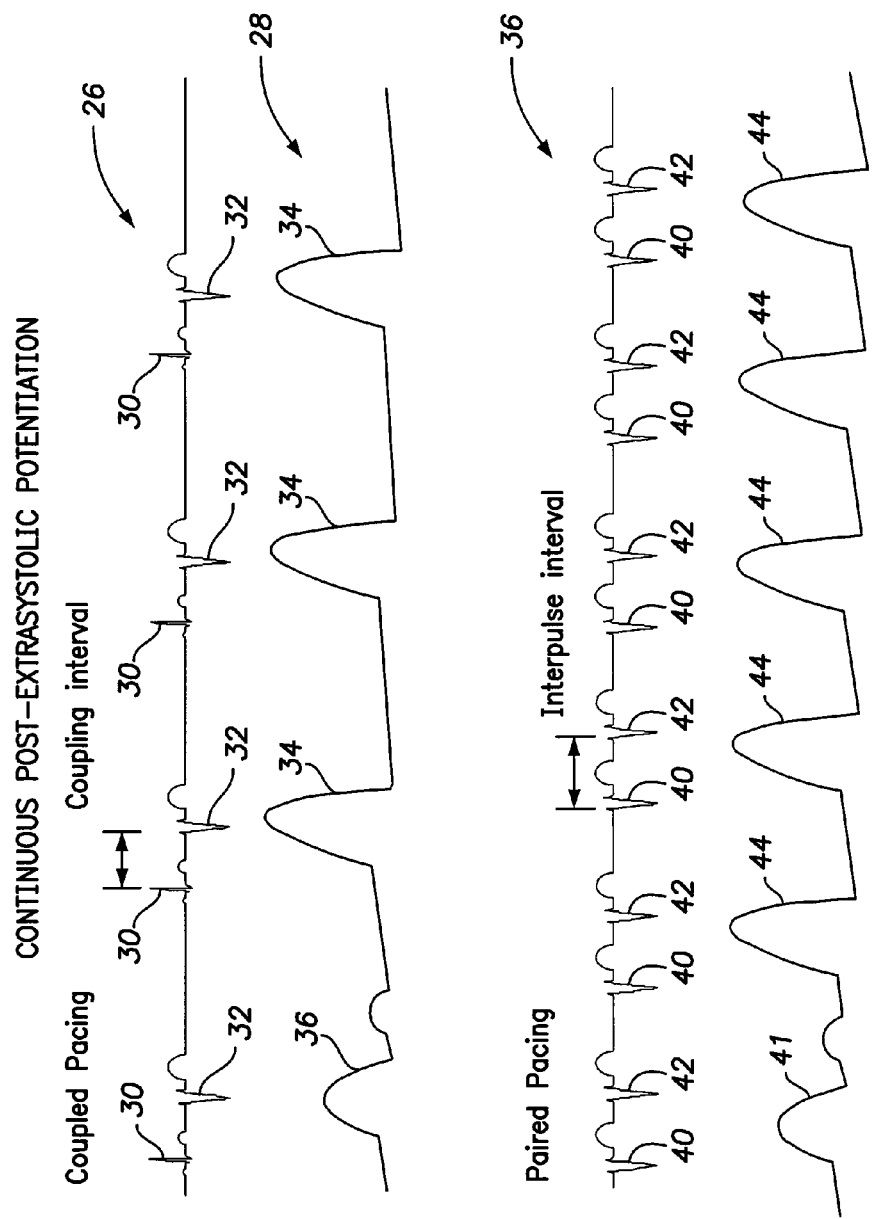
FIG. 2 is a graph illustrating continuous paired and coupled PESP techniques in accordance with the prior art.
Figure 3:
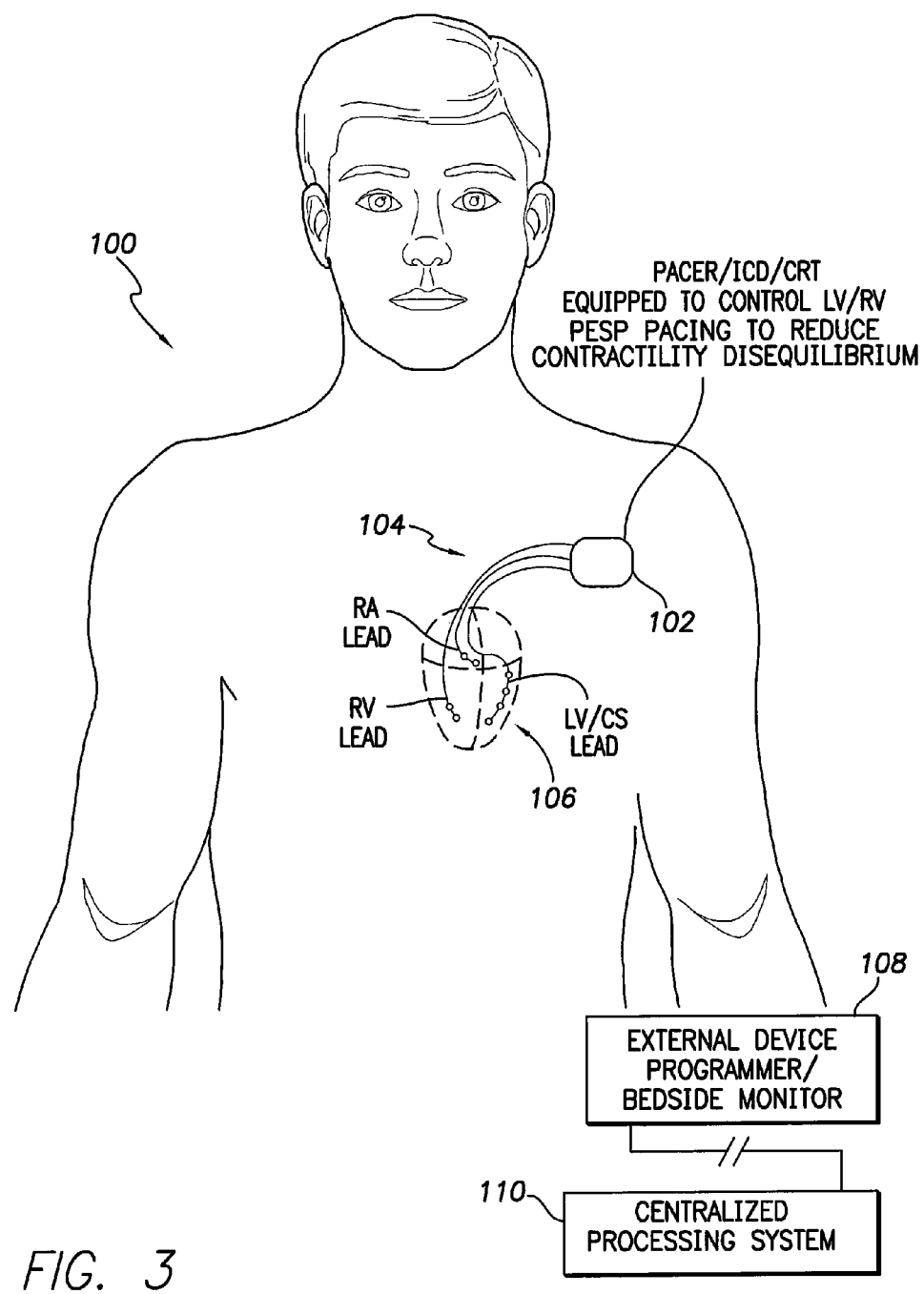
FIG. 3 illustrates components of an implantable medical system having a pacemaker, ICD or CRT device equipped to control paired PESP pacing to reduce contractility disequilibrium in accordance with an exemplary embodiment of the invention.

FIG. 3 illustrates an implantable medical system 100 capable of delivering paired PESP pacing while separately controlling the LV and RV interpulse intervals to reduce contractility disequilibrium, particularly for use within patients with one ventricle weakened by ischemia or CHF. In this particular example, the implantable medical system 100 includes a pacer/ICD/CRT 102 or other implantable cardiac rhythm management device equipped with a set of cardiac sensing/pacing leads 104 implanted on or within the heart of the patient, including a multi-pole LV lead implanted via the coronary sinus (CS.) In FIG. 3, a stylized representation of the set of leads is provided. A more accurate illustration of the leads is provided in FIG. 11, discussed below. To illustrate the multi-pole configuration of the LV lead, a set of electrodes 106 is shown distributed along the LV lead.

In the examples described herein, a quad-pole (or "quadrapolar" or "quadripolar") LV lead is employed, such as the Quartet™ lead provided by St Jude Medical. Other suitable leads may instead be employed, including leads with more or fewer electrodes, depending upon the needs of the particular implementation. In many cases, the LV lead will instead be a bipolar lead. Also, as shown, an exemplary RV lead is provided that includes a bipolar RV tip/ring electrode pair. An RA lead is also provided that includes a bipolar RA tip/ring pair. (Although not shown in FIG. 3, the RA lead might additionally include an LAP sensor for transseptal implant. See, FIG. 11. Alternatively, yet another separate lead may be provided for implant of the LAP sensor.) Other electrodes of various sizes and shapes may be additionally or alternatively provided, such as various coil electrodes for delivering shock therapy. Although identified as a "pacer/ICD/CRT" in FIG. 3, it should be understood that device 102 can be any suitably-equipped implantable medical device, such as a standalone pacemaker, ICD or CRT device, including CRT-D and CRT-P devices. In the following, for brevity, device 102 will be referred to simply as a pacer/CRT.

Figure 4:
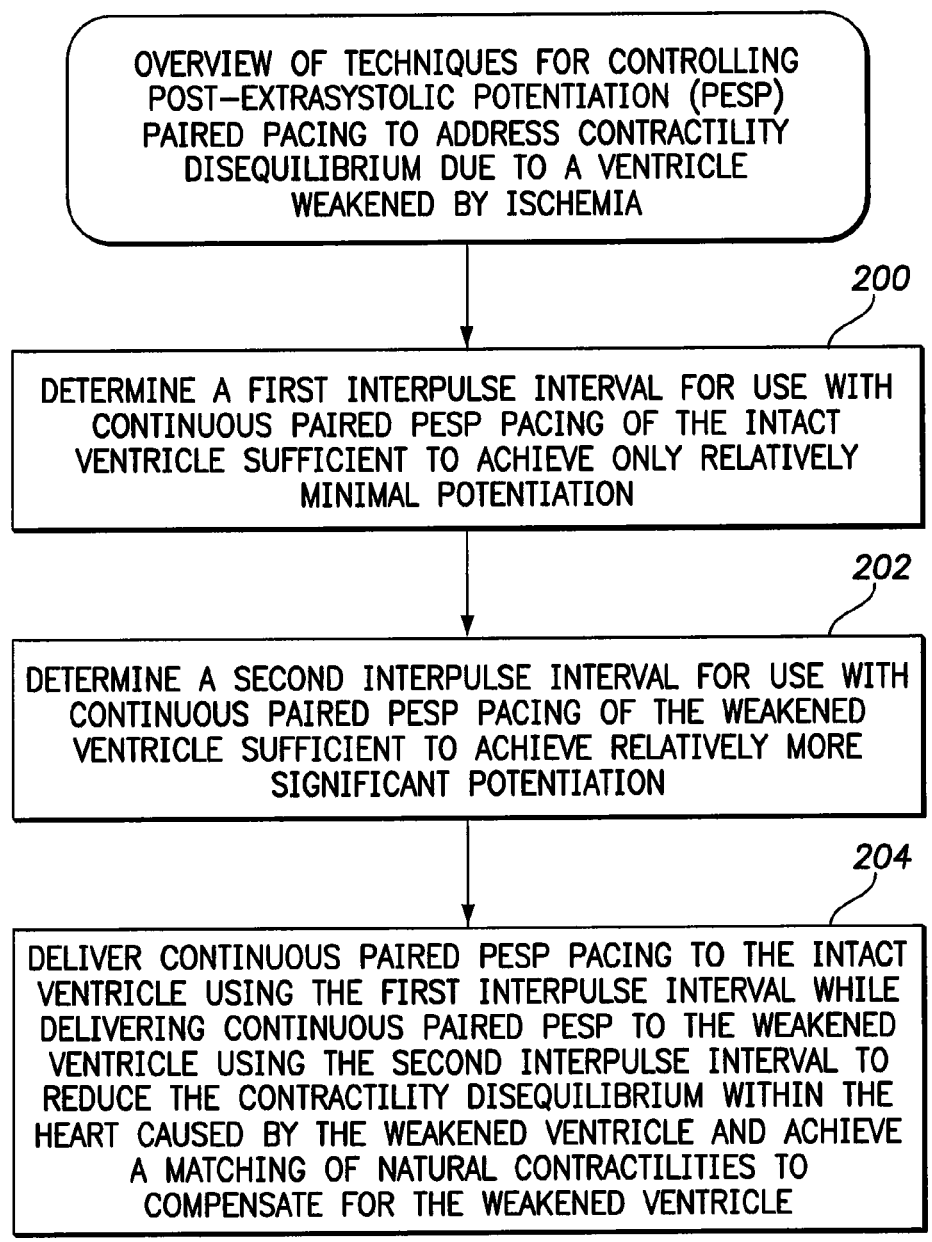
FIG. 4 summarizes a general technique for controlling paired PESP pacing to reduce disequilibrium that may be performed by the system of FIG. 3.

FIG. 4 broadly summarizes techniques employed by the pacer/CRT of FIG. 3 (or other suitably-equipped systems) for controlling paired pacing to address contractility disequilibrium due to a ventricle weakened by ischemia. Beginning at step 200, the pacer/CRT determines a first interpulse interval for use with continuous paired PESP pacing of the intact ventricle sufficient to achieve only relatively minimal potentiation within the ventricle. For example, the device may determine the duration of the absolute refractory period and then set the first interpulse interval slightly longer than the absolute refractory period to thereby time the delivery of the second pulse of the pair just outside the absolute refractory period to trigger minimal potentiation within that ventricle. At step 202, the pacer/CRT determines a second interpulse interval for use with continuous paired PESP pacing of the weakened ventricle sufficient to achieve relatively more significant potentiation, and preferably maximum potentiation, in that ventricle. For example, the device may deliver test pulses at various differing intervals while assessing the degree of potentiation achieved so as to determine the interpulse interval that substantially maximizes that potentiation. The degree of potentiation may be assessed, e.g., based on pressure measurements if the device is equipped with suitable LV or RV pressure sensors. Alternatively, the device may input information from an external programmer originally generated using echocardiography or other hemodynamic assessment techniques to determine the interpulse interval needed maximize potentiation.

At step 204, the pacer/CRT delivers continuous paired PESP pacing to the intact ventricle using the first interpulse interval while delivering continuous paired PESP to the weakened ventricle using the second interpulse interval to reduce the contractility disequilibrium within the heart caused by the weakened ventricle and to achieve a matching of natural contractilities to compensate for the weakened ventricle. Thus, the device exploits the differing degree of potentiation that can be achieved by separately adjusting LV and RV interpulse intervals, i.e. the device exploits the recognition that the degree of potentiation achieved via PESP depends substantially only on the timing of the extrasystole and that timing can be set to differ for the RV and the LV.

Figure 5:
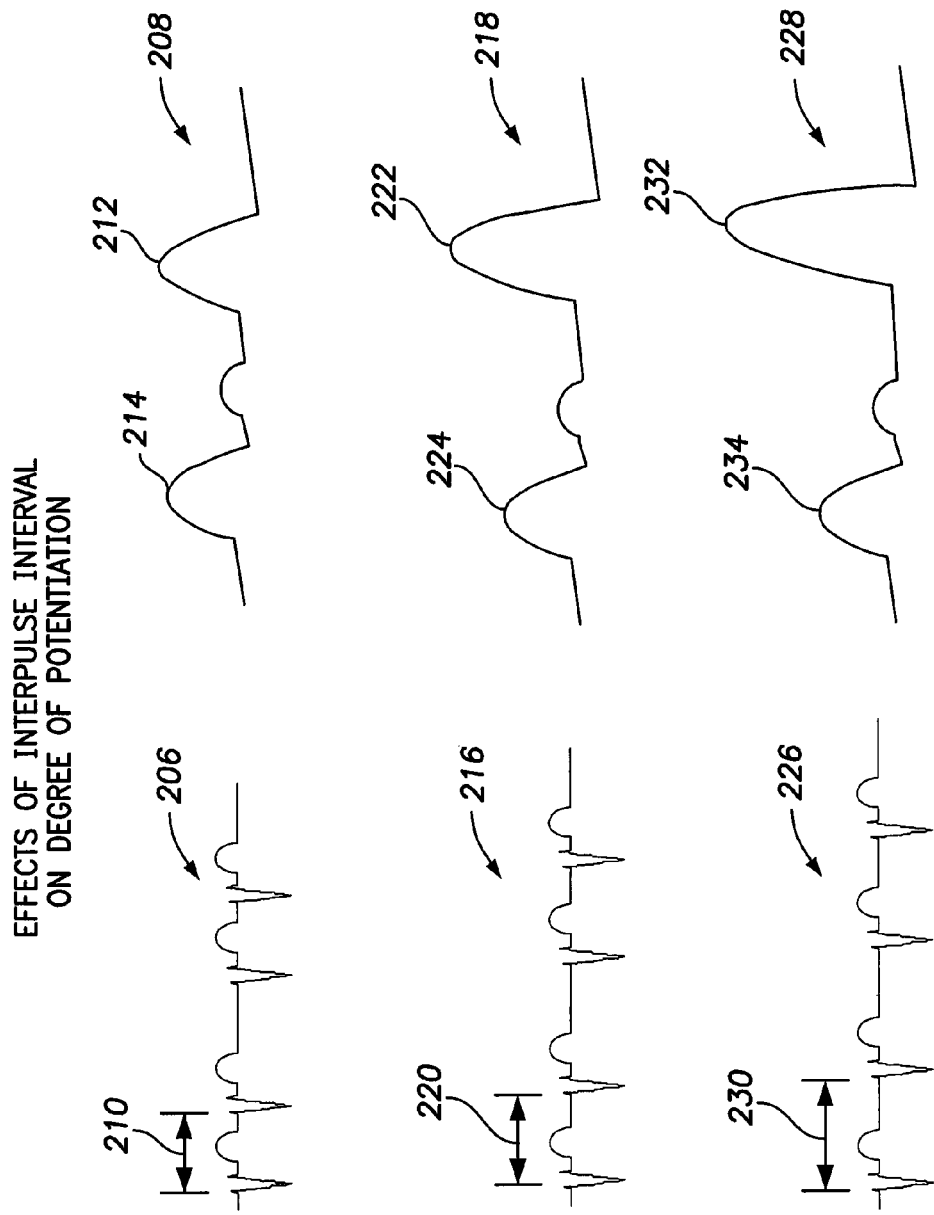
FIG. 5 is a graph illustrating changes in potentiation achieved by changing the interpulse interval, which is exploited by the technique of FIG. 4.

FIG. 5 illustrates the effects of interpulse interval on PESP. A first pair of traces illustrates the effects of a short interpulse interval by way of an ECG 206 and a ventricular pressure graph 208. The short interpulse interval 210 leads to potentiation sufficient to yield a ventricular pressure 212 that is somewhat greater than an unpotentiated pressure level 214 but not significantly so. A second pair of traces illustrates the effects of a longer interpulse interval by way of ECG 216 and ventricular pressure graph 218. The longer interpulse interval 220 leads to potentiation sufficient to yield a greater increase in ventricular pressure 222 than with the shorter interpulse interval of trace 208. A third pair of traces illustrates the effects of a still longer interpulse interval by way of ECG 226 and ventricular pressure graph 228. Interpulse interval 230 leads to potentiation sufficient to yield a ventricular pressure 232 that is significantly greater than can be achieved with a short interpulse interval. As such, by adjusting the interpulse interval, the degree of potentiation can be likewise be adjusted. A short interpulse interval may be used within the intact ventricle; a longer one in the weakened ventricle.

Exemplary Embodiments

Figure 6:
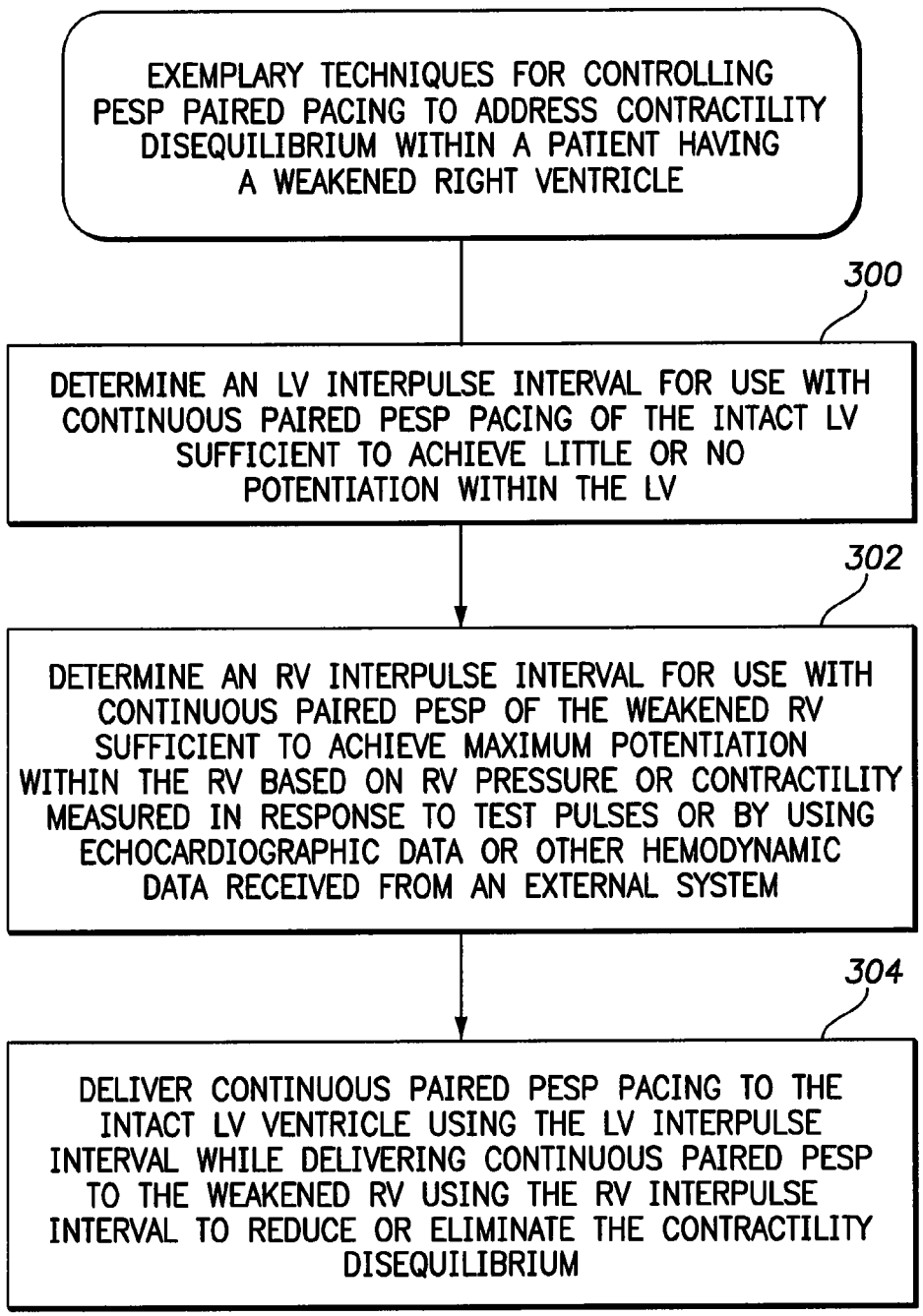
FIG. 6 illustrates an exemplary technique for controlling paired PESP in accordance with the general technique of FIG. 4 for use with patients having a weakened RV and an intact LV.
Figure 7:
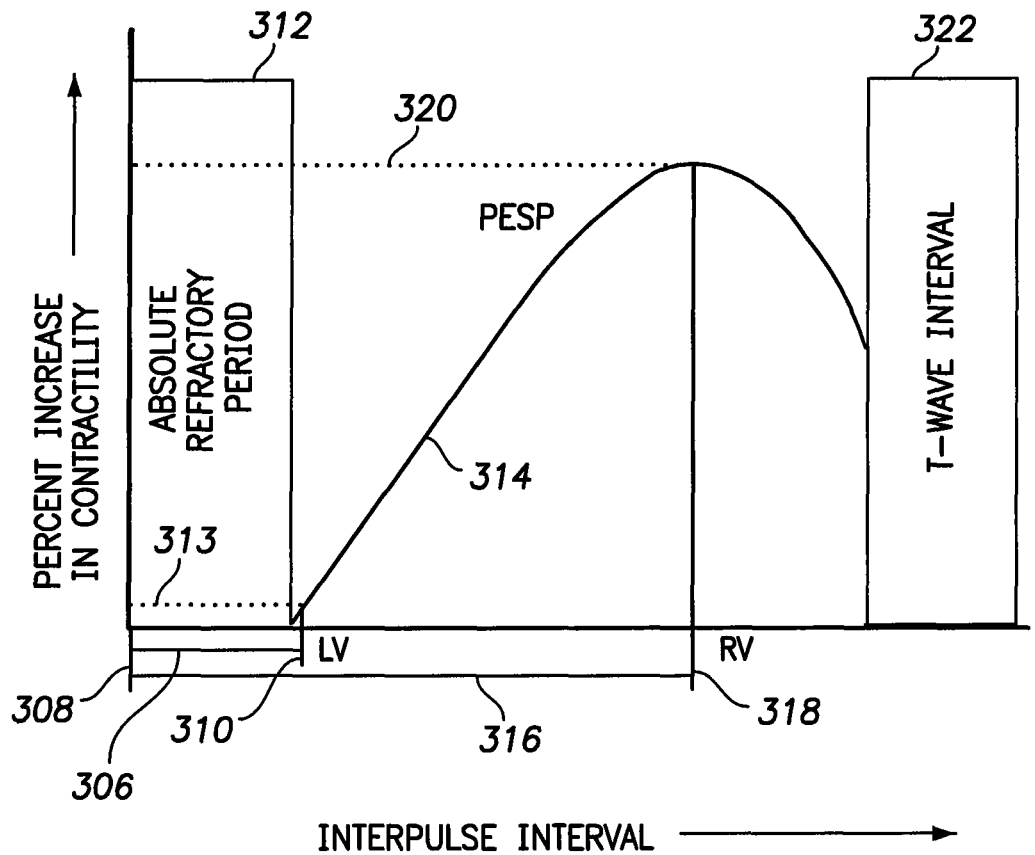
FIG. 7 is a graph illustrating exemplary LV and RV interpulse intervals exploited by the technique of FIG. 6 and the resulting potentiation.

FIGS. 6 and 7 illustrate exemplary techniques where the RV is weakened by ischemia or infarction but the LV is largely intact. Beginning at step 300 of FIG. 6, the device determines or inputs an LV interpulse interval for use with continuous paired PESP pacing of the intact LV sufficient to achieve little or no potentiation within the LV. This may be determined by first determining the length of the absolute refractory period, which may depend on the paired pacing rate, and then setting the LV interpulse interval slightly greater than the absolute refractory period so as to achieve little or no potentiation in the LV. At step 302, the device determines or inputs an RV interpulse interval for use with continuous paired PESP of the weakened RV sufficient to achieve maximum potentiation within the RV. For example, the device may deliver test pulses at various RV interpulse intervals (and while holding the LV interpulse interval constant) while assessing the degree of potentiation in the RV so as to determine the RV interpulse interval that substantially maximizes RV potentiation. The degree of potentiation in the RV may be assessed based on the resulting RV pressure, which may be assessed using suitable sensors or proxies. See, for example, U.S. Patent Application 2002/0058969 of Noren et al., entitled "Implantable Medical Device for Measuring Ventricular Pressure."

Additionally or alternatively, depending upon the capabilities of the device, the degree of potentiation in the RV may be assessed based on RV contractility as measured or estimated using on suitable sensors or proxies. Techniques for detecting cardiac contractility are discussed in, e.g., U.S. Pat. No. 6,788,970 to Park et al., U.S. Pat. No. 6,208,900 to Ecker et al. and U.S. Pat. No. 4,485,813 to Anderson et al. Heart sound waves can also be used to determine contractility and other related parameters (e.g., stroke volume, blood pressure and dP/dt), as disclosed in U.S. Pat. No. 6,044,299 to Nilsson. IEGM signals may also provide a basis for determining contractility. See, for example, U.S. Pat. No. 4,759,366 to Callaghan. Impedance measurements of blood in the heart can also been employed to derive contractility of the myocardium. See, U.S. Pat. No. 4,884,576 to Alt and U.S. Pat. No. 4,535,774 to Olsen. Also, the rate of change in impedance (dZ/dt) has been shown to correspond to contractility. See, for example, U.S. Pat. No. 4,733,667 to Olive et al. and U.S. Pat. No. 5,800,467 to Park et al. In some examples, surrogates for myocardial contractility are derived from cardiac pressure signals or photoplethysmography (PPG) signals. See, for example, techniques described in published U.S. Patent Application No. 2010/0234906 of Koh, entitled "System and Method for Controlling Rate-Adaptive Pacing based on a Cardiac Force-Frequency Relation detected by an Implantable Medical Device."

The contractility assessment techniques of the aforementioned patents may need to be modified, where appropriate, to assess the contractility of just the RV so as to allow for maximizing the potentiation of the RV (as opposed to the LV.) Also, as noted, the degree of potentiation achieved using certain interpulse intervals may be assessed based on information generated using echocardiography or other hemodynamic assessment techniques performed by an external system and then input into the device.

At step 304, the device then delivers continuous paired PESP pacing to the intact LV ventricle using the LV interpulse interval determined at step 300 while delivering continuous paired PESP to the weakened RV using the RV interpulse interval determined at step 304 to reduce or eliminate the contractility disequilibrium between the RV and LV.

FIG. 7 illustrates exemplary LV and RV interpulse intervals for use in cases where the LV is intact but the RV is weakened. Briefly, an LV interpulse interval 306 is shown between the time 308 when an initial pulse of a pulse pair is delivered to the LV and the time 310 when the paired LV pulse is delivered. As can be seen, the LV interpulse interval is set so that the second pulse is delivered at a time 310 just following the end of the absolute refractory period 312. The degree of potentiation achieved in the LV by this short interpulse interval is minimal and is shown by line 313, which intersects with PESP curve 314. A longer RV interpulse interval 316 is shown between time 308 when an initial pulse is delivered to the RV and the time 318 when the paired RV pulse is delivered. The RV interpulse interval is set so that the second pulse is timed to maximize RV potentiation. The degree of potentiation achieved in the RV by this longer interpulse interval is maximum, as shown by line 320. Note that, following the time of maximum potentiation, the PESP curve diminishes so that pulses delivered after that point would result in less potentiation. That is, still greater increases in the interpulse interval starts to produce fewer rewards, and eventually, with further increases, pacing with longer interpulse intervals will not only cause a decrease in the potentiation but will occur during the dangerous upward rise of the T-wave. The first portion of the T-wave interval is shown in the figure by way of block 322. Note also that, in the example of FIG. 7, the first pulse of the LV pair and the first pulse of the RV pair are delivered at the same time, i.e. VV=0. In other examples, an interventricular delay may also be used, i.e. VV≠0.

Figure 8:
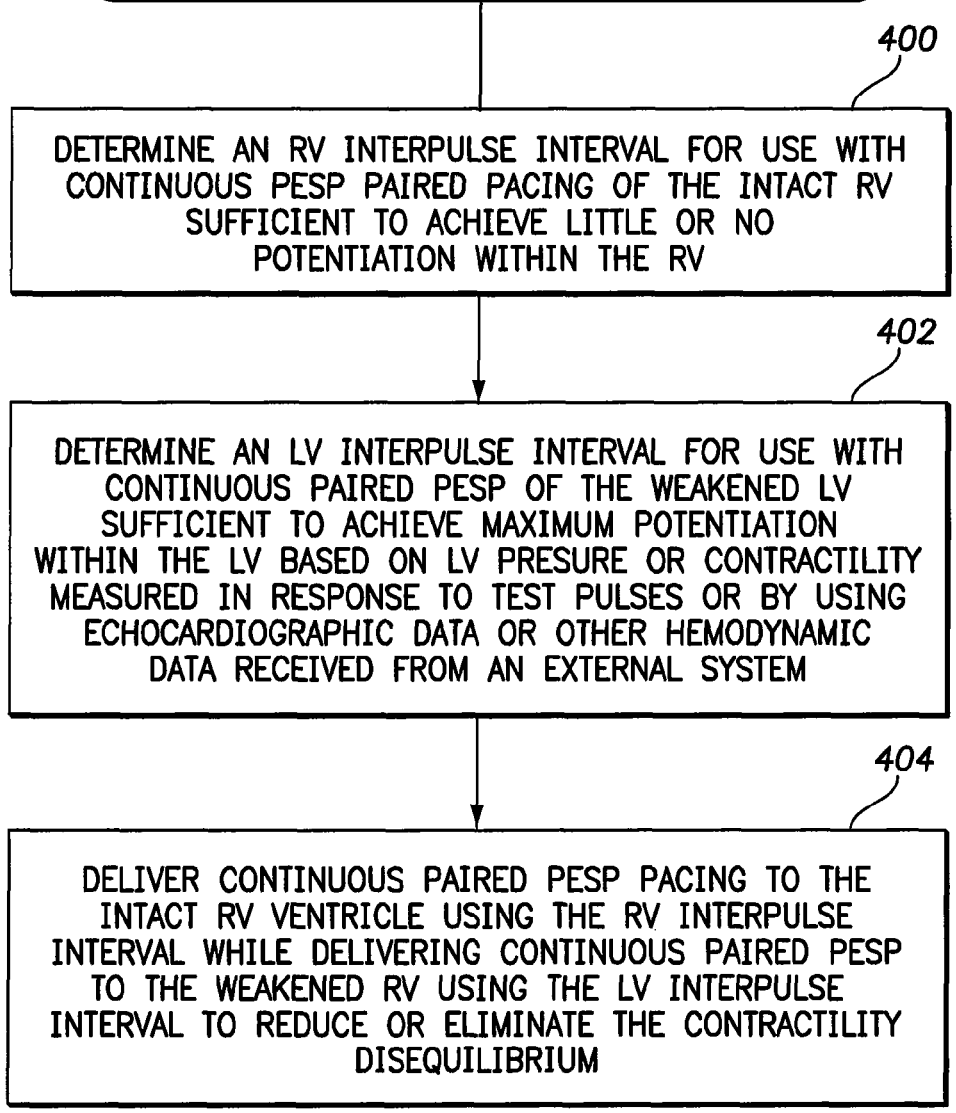
FIG. 8 illustrates another exemplary technique for controlling paired PESP in accordance with the general technique of FIG. 4 but for use with patients having a weakened LV and an intact RV.
Figure 9:
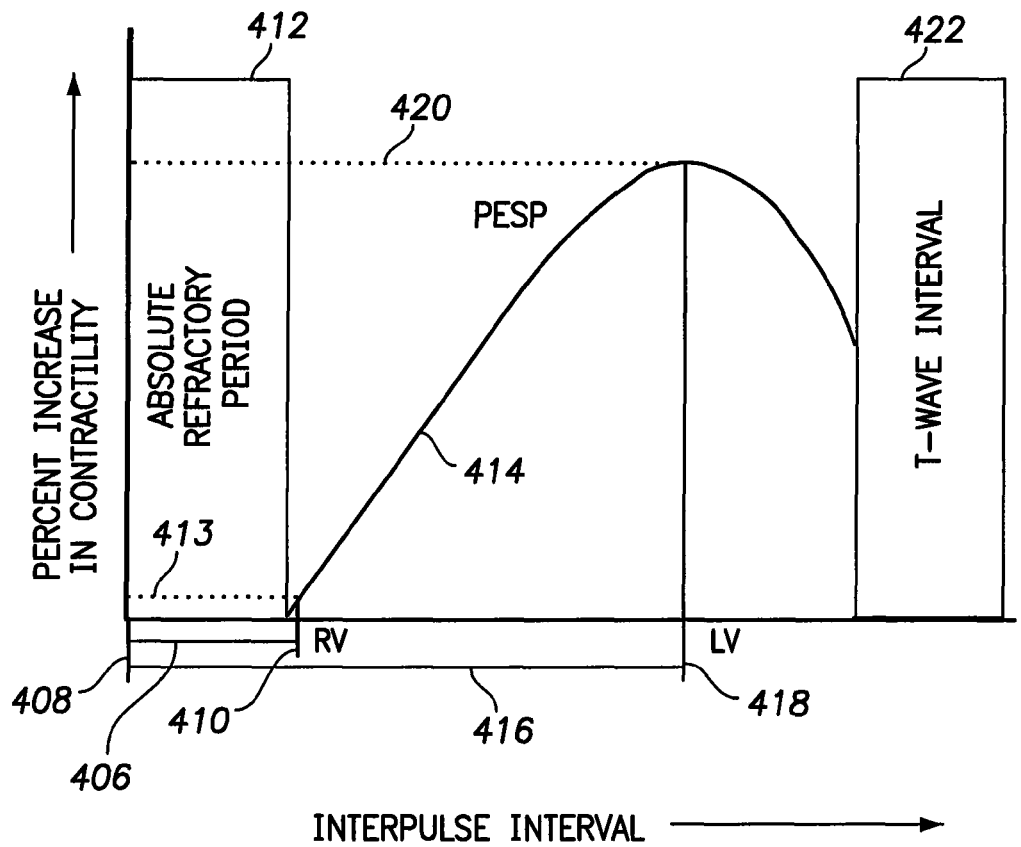
FIG. 9 is a graph illustrating exemplary LV and RV interpulse intervals exploited by the technique of FIG. 8 and the resulting potentiation.

FIGS. 8 and 9 illustrate exemplary techniques where the LV is weakened but the RV is largely intact. Many of the steps of these techniques are similar to those of FIGS. 6 and 7 and hence will only briefly be described. Beginning at step 400 of FIG. 8, the device determines or inputs an RV interpulse interval for use with continuous paired PESP pacing of the intact RV sufficient to achieve little or no potentiation within the RV. At step 402, the device determines or inputs an LV interpulse interval for use with continuous paired PESP of the weakened LV sufficient to achieve maximum potentiation within the LV. For example, the device may deliver test pulses at various LV interpulse intervals (and while holding the RV interpulse interval constant) while assessing the degree of potentiation in the LV so as to determine the LV interpulse interval that substantially maximizes LV potentiation. The degree of potentiation in the LV may be determined based on the resulting LV pressure, which may be assessed using suitable sensors or proxies. See, for example, U.S. Pat. No. 6,666, 826 to Salo et al., entitled "Method and Apparatus for Measuring Left Ventricular Pressure" and U.S. Pat. No. 7,437,192 to Gill et al., entitled "System and Method for Detecting Heart Failure and Pulmonary Edema based on Ventricular End-Diastolic Pressure using an Implantable Medical Device."

Additionally or alternatively, depending upon the capabilities of the device, the degree of potentiation in the LV may be assessed based on LV contractility as measured or estimated using suitable sensors or proxies, such as those discussed in the patent documents cited above in connection with RV contractility. The contractility assessment techniques may need to be modified, where appropriate, to assess the contractility of just the LV so as to allow for maximizing the potentiation of the LV (as opposed to the RV.) Also, as noted, the degree of potentiation achieved using certain interpulse intervals may be assessed based on information generated using echocardiography or other hemodynamic assessment techniques performed by an external system and then input into the device.

At step 404, the device then delivers continuous paired PESP pacing to the intact RV ventricle using the RV interpulse interval determined at step 400 while delivering continuous paired PESP to the weakened LV using the LV interpulse interval determined at step 404 to reduce or eliminate the contractility disequilibrium between the RV and LV.

FIG. 9 illustrates exemplary LV and RV interpulse intervals for use in cases where the LV is weakened but the RV is intact. Briefly, an RV interpulse interval 406 is shown between the time 408 when an initial pulse of a pulse pair is delivered to the RV and the time 410 when the paired RV pulse is delivered. The RV interpulse interval is set so that the second pulse is delivered at a time 410 just following the end of the absolute refractory period 412. The degree of potentiation achieved in the RV by this short interpulse interval is minimal and is shown by line 413, which intersects with PESP curve 414. A longer LV interpulse interval 416 is shown between the time 408 when an initial pulse is delivered to the LV and the time 418 when the paired LV pulse is delivered. The LV interpulse interval is set so that the second pulse is timed to maximize LV potentiation. The degree of potentiation achieved in the LV by this longer interpulse interval is maximum, as shown by line 420. The figure also shows the time period for the T-wave interval 422, during which no pulses should be delivered. As in the example of FIG. 7, the first pulse of the LV pair and the first pulse of the RV pair are delivered at the same time, i.e. VV=0. In other examples, an interventricular delay may also be used, i.e. VV≠0.

As noted above, in the case where the LV is weakened, by independently increasing the output of the LV relative to the RV, the LAP will tend to decrease and pulmonary congestion will then also tend to decrease. The risk of pulmonary edema would then tend to decrease. More importantly, in time, the heart should remodel, with a decrease in dilatation and mitral regurgitation. It is expected that, when depressed left ventricular contractility is improved by, e.g., 50% with paired pacing, the mean arterial blood pressure, stroke volume, and left ventricular ejection fraction will all increase, and the left atrial pressure will be reduced along with a reduction in the left ventricular dilatation.

Figure 10:
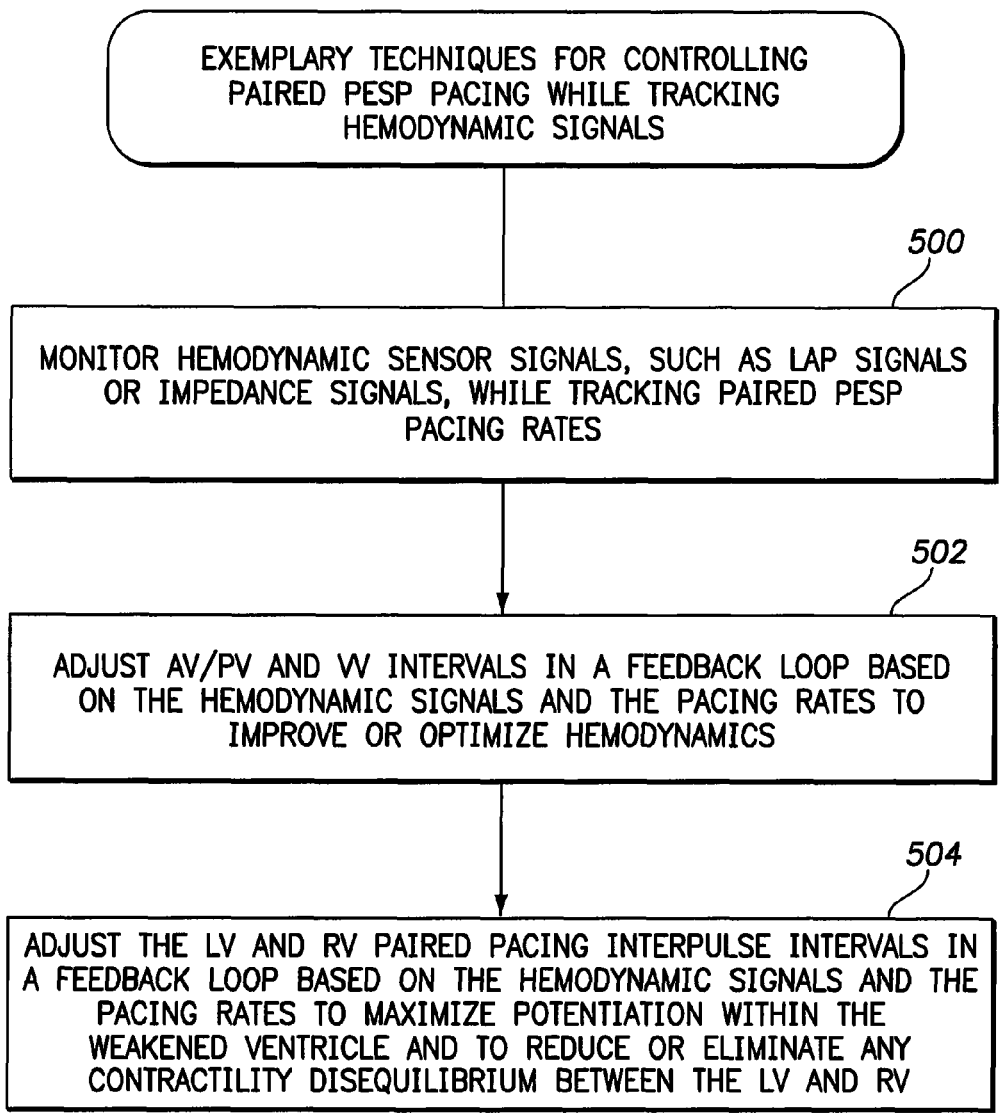
FIG. 10 illustrates an exemplary technique for use with the general technique of FIG. 4, wherein a physiological sensor is used to control the LV and RV interpulse intervals in a feedback loop.

FIG. 10 summarizes techniques for controlling paired PESP pacing based on hemodynamic or physiological sensor signals in a feedback loop to maximize potentiation in a weakened ventricle and to generally improve hemodynamics. At step 500, the pacer/CRT monitors hemodynamic sensor signals, such as LAP signals or impedance signals, while tracking paired PESP pacing rates. LAP sensors are discussed in, for example, U.S. Published Patent Application 2003/0055345 of Eigler et al., entitled "Permanently Implantable System and Method for Detecting, Diagnosing and Treating Congestive Heart Failure." Techniques for detecting LAP that do not necessarily require an LAP sensor (such as by using cardiogenic impedance as a proxy) are discussed in U.S. Provisional Patent Application No. 60/787,884 of Wong et al., entitled, "Tissue Characterization Using Intracardiac Impedances with an Implantable Lead System," filed Mar. 31, 2006 and in U.S. patent application Ser. Nos. 11/558,101; 11/557, 851; 11/557,870; 11/557,882; and 11/558,088, each entitled "Systems and Methods to Monitor and Treat Heart Failure Conditions," of Panescu et al. See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device." See, also, U.S. patent application Ser. Nos.

11/779,350 and 11/779,380, of Wenzel et al., filed Jul. 18, 2007, both entitled "System and Method for Estimating Cardiac Pressure based on Cardiac Electrical Conduction delays using an Implantable Medical Device."

At step 502, the pacer/CRT adjusts AV/PV and VV intervals in a feedback loop based on the hemodynamic signals and the pacing rates to improve or optimize hemodynamics. That is, the parameters are adjusted (periodically or in real time) while monitoring the hemodynamic signals to determine parameters sufficient to improve or optimize hemodynamics as quantified by a suitable proxy such as LAP (where a lower LAP is preferred.) Note that some of the aforementioned patent documents set forth techniques for adjusting AV/PV and VV intervals based on LAP, though not necessarily in the context of paired PESP pacing. At step 504, the pacer/CRT then also adjusts the LV and RV paired pacing interpulse intervals in a feedback loop based on the hemodynamic signals and the pacing rates to maximize potentiation within the weakened ventricle and to reduce or eliminate any contractility disequilibrium between the LV and RV. For example, the interpulse intervals may be adjusted (periodically or in real time) via feedback to yield values sufficient to minimize any contractility disequilibrium or to further minimize LAP. Techniques for assessing chamber disequilibrium are described in U.S. patent application Ser. No. 13/007,424 of Gutfinger et al., filed Jan. 14, 2011, entitled "Systems and Methods for Exploiting Near-Field Impedance and Admittance for use with Implantable Medical Devices."

By employ feedback loops, the AV/PV, VV and interpulse PESP intervals may be advantageously adjusted to improve hemodynamics, reduce disequilibrium, maximize potentiation within a weakened ventricle, or achieve other desirable benefits, alone or under the supervision of a clinician. In some examples, the implantable device operates automatically based on LAP to set the parameters in an attempt to lower LAP to a target level set by the clinician. For feedback techniques, see also U.S. Pat. No. 5,213,098 of Bennett et al., entitled "Post-Extrasystolic Potentiation Stimulation with Physiologic Sensor Feedback," which discloses, inter alia, a cardiac pacing energy stimulator for applying paired and/or triggered pacing stimulation pulses to the right atrium and/or ventricle incorporating one or more sensors, such as a venous oxygen saturation, ventricular, atrial, or arterial blood pressure, or intracardiac or systemic blood flow sensor, and signal processing circuitry for controlling the frequency of or number of heart cycles between periodic delivery of triggered or paired pacing to induce PESP for the treatment of congestive heart failure or other cardiac dysfunctions.

Thus, various techniques have been described herein for independently adjusting dual-site ventricular paired PESP interpulse intervals to reduce contractility disequilibrium or achieve other advantageous goals. The various techniques described herein are applicable to a wide variety of systems, including systems equipped for multi-site LV (MSLV) pacing. For MSLV, see, for example, the techniques described in U.S. Patent Application 2011/0022112 of Min, entitled "Systems and Methods for Determining Ventricular Pacing Sites for use with Multi-Pole Leads." For multi-site implementations, the particular quadpolar electrode(s) of the LV lead to be used for delivering the paired PESP to the LV can be selected by the clinician based on the most efficacious timing for improving cardiac contractility. In addition to timing for single-sided contractility improvement, the timing and site(s) of pacing could prove critical to prevent arrhythmia development if there are functional electrophysiological rotors in place.

It should be understood that the "optimal" interpulse intervals obtained using the techniques described herein are not necessarily absolutely optimal in a given quantifiable or mathematical sense. What constitutes "optimal" depends on the criteria used for judging the resulting performance, which can be subjective in the minds of some clinicians. The interpulse intervals determined by the techniques described herein represent, at least, "preferred" interpulse intervals. Clinicians may choose to adjust or alter the interpulse intervals for particular patients, at their discretion.

For the sake of completeness, an exemplary pacer/CRT will now be described, which includes components for performing the functions and steps already described, as well as components for controlling CRT.

Exemplary Pacer/CRT

Figure 11:
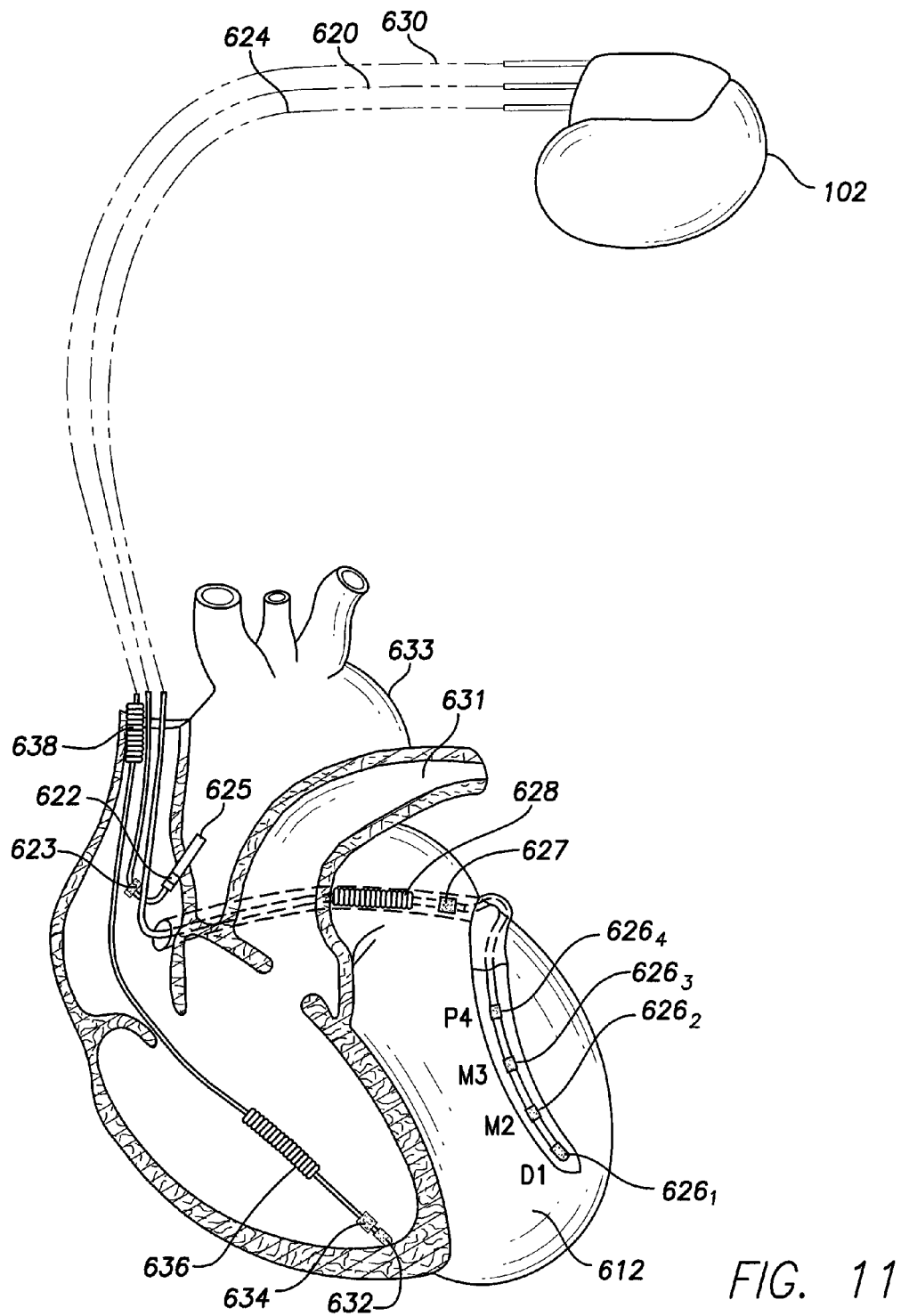
FIG. 11 is a simplified, partly cutaway view, illustrating the device of FIG. 3 along with a set of leads implanted into the heart of the patient.
Figure 12:
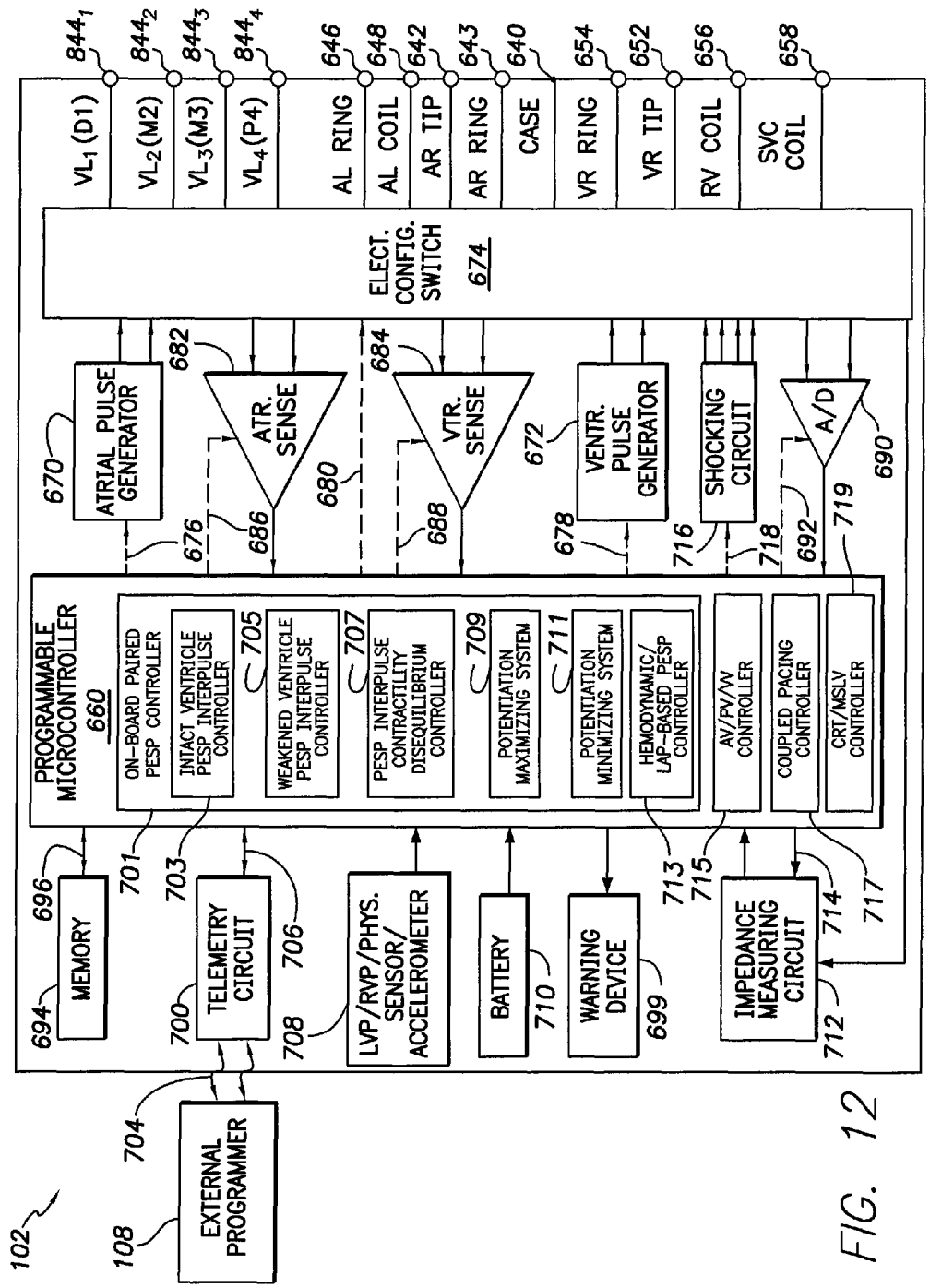
FIG. 12 is a functional block diagram of the pacer/CRT of FIG. 11, illustrating basic circuit elements that provide cardioversion, defibrillation and/or pacing stimulation in the heart and particularly illustrating components for performing or controlling the various techniques of FIGS. 4-10.

With reference to FIGS. 11 and 12, a description of an exemplary pacer/CRT will now be provided. FIG. 11 provides a simplified block diagram of the pacer/CRT, which is a dual-chamber stimulation device capable of treating both fast and slow arrhythmias with stimulation therapy, including cardioversion, defibrillation, and pacing stimulation, and also capable of controlling PESP to address contractility disequilibrium, as discussed above. To provide atrial chamber pacing stimulation and sensing, pacer/CRT 102 is shown in electrical communication with a heart 612 by way of a right atrial lead 620 having an atrial tip electrode 622 and an atrial ring electrode 623 implanted in the atrial appendage. The RA lead also includes an LAP sensor 625 (or other hemodynamic or physiological sensor), which is transseptally positioned between the RA and the LA. For a description of a transseptally implanted physiological sensor, see for example, U.S. patent Ser. No. 11/927,026, filed Oct. 29, 2007, entitled "Systems and Methods for Exploiting Venous Blood Oxygen Saturation in combination with Hematocrit or Other Sensor Parameters for use with an Implantable Medical Device."

Pacer/CRT 102 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/CRT 102 is coupled to a multi-pole LV lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, the exemplary LV lead 624 is designed to receive atrial and ventricular cardiac signals and to deliver left ventricular pacing therapy using a set of four left ventricular electrodes $626_1$ (D1), $626_2$ (M2), $626_3$ (M3), and $626_4$ (P4), left atrial pacing therapy using at least a left atrial ring electrode 627, and shocking therapy using at least a left atrial coil electrode 628. The $626_1$ LV electrode may also be referred to as a "tip" or "distal" LV electrode. The $626_4$ LV electrode may also be referred to as a "proximal" LV electrode. In other examples, more or fewer LV electrodes are provided. Although only three leads are shown in FIG. 11, it should also be understood that additional leads (such as a separate lead for an LAP sensor) might be used and/or additional electrodes might be provided on the leads already shown, such as additional electrodes on the RV lead.

A simplified block diagram of internal components of pacer/CRT 102 is shown in FIG. 12. While a particular pacer/CRT is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/CRT 102, shown schematically in FIG. 12, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, $644_1$-$644_4$, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes a left ventricular tip terminal ($VL_1$ (D1)) $644_1$ and additional LV electrode terminals $644_2$-$644_4$ for the other LV electrodes of the LV lead. Although not show, an additional terminal may be used for receiving signals from the LAP sensor.

The connector also includes a left atrial ring terminal ($A_L$ RING) 646 and a left atrial shocking terminal ($A_L$ COIL) 648, which are adapted for connection to the left atrial ring electrode 627 and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal (RV COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/CRT 102 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 12, an atrial pulse generator 670 and a ventricular pulse generator 672 generate pacing stimulation pulses for delivery by the right atrial lead 620, the right ventricular lead 630, and/or the LV lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.), and interpulse PESP intervals, as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 682 and ventricular sensing circuits 684 may also be selectively coupled to the right atrial lead 620, LV lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/CRT 102 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/CRT 102 utilizes the atrial and ventricular sensing circuits, 682 and 684, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 16. The data acquisition system 690 is coupled to the right atrial lead 620, the LV lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/CRT 102 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/CRT 102 may be non-invasively programmed into the memory 694 through a telemetry circuit 700 in telemetric communication with the external device 108, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/CRT 7 (as contained in the microcontroller 660 or memory 694) to be sent to the external device 702 through an established communication link 704. Pacer/CRT 102 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, VV delay, etc.) at which the atrial and ventricular pulse generators, 670 and 672, generate stimulation pulses. While shown as being included within pacer/CRT 102, it is to be understood that the physiologic sensor 708 may also be external to pacer/CRT 102, yet still be implanted within or carried by the patient. The sensor may be additionally equipped to sense LVP or RVP. A common type of rate responsive sensor is an activity sensor incorporating an accelerometer or a piezoelectric crystal, which is mounted within the housing 640 of pacer/CRT 102. Other types of physiologic sensors are known, for example, sensors that sense the oxygen content of blood, respiration rate and/or minute ventilation, pH of blood, ventricular gradient, etc.

The pacer/CRT additionally includes a battery 710, which provides operating power to all of the circuits shown in FIG. 12. The battery 710 may vary depending on the capabilities of pacer/CRT 102. If the system only provides low voltage therapy, a lithium iodine or lithium copper fluoride cell typically may be utilized. For pacer/CRT 102, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 12, pacer/CRT 102 is shown as having an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, and detecting cardiogenic impedance, etc. The impedance measuring circuit 712 is advantageously coupled to the switch 674 so that any desired electrode may be used.

In the case where pacer/CRT 102 is intended to operate as an ICD device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-9 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 6-40 joules or more), delivered asynchronously (since R-waves may be too disorganized), and pertaining exclusively to the treatment of fibrillation. Accordingly, the microcontroller 660 is capable of controlling synchronous or asynchronous delivery of shocking pulses.

An internal warning device 699 may be provided for generating perceptible warning signals to the patient via vibration, voltage or other methods.

Insofar as PESP is concerned, the microcontroller includes an on-board paired PESP controller 701 operative to perform or control all or some of the techniques described above. On-board controller 701 includes an intact ventricle PESP interpulse controller 703 operative to determine the first interpulse interval for use with paired PESP pacing of the intact ventricle sufficient to achieve little or no potentiation. On-board controller 701 also includes a weakened ventricle PESP interpulse controller 705 operative to determine the second interpulse interval for use with paired PESP pacing of the weakened ventricle sufficient to maximize potentiation. A PESP interpulse contractility disequilibrium controller 707 is operative to deliver paired PESP pacing to the intact ventricle using the first interpulse interval while delivering paired PESP to the weakened ventricle using the second interpulse interval to reduce contractility disequilibrium within the heart caused by the weakened ventricle. A potentiation maximizing system 709 is exploited to determine interpulse intervals needed to maximize potentiation for use in the weakened ventricle. A potentiation minimizing system 711 is exploited to determine interpulse intervals needed to minimize potentiation for use in the intact ventricle. A hemodynamic/LAP-based PESP controller 713 is used to adjust the interpulse intervals to improve or optimize hemodynamic parameters such as LAP. An AV/PV/VV controller 715 is used to set or optimize AV/PV and W delays. A coupled pacing controller 717 may also be provided to selectively apply coupled pacing in circumstance where it might be warranted. CRT and MSLV are controlled by a CRT/MSLV controller 719.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 13:
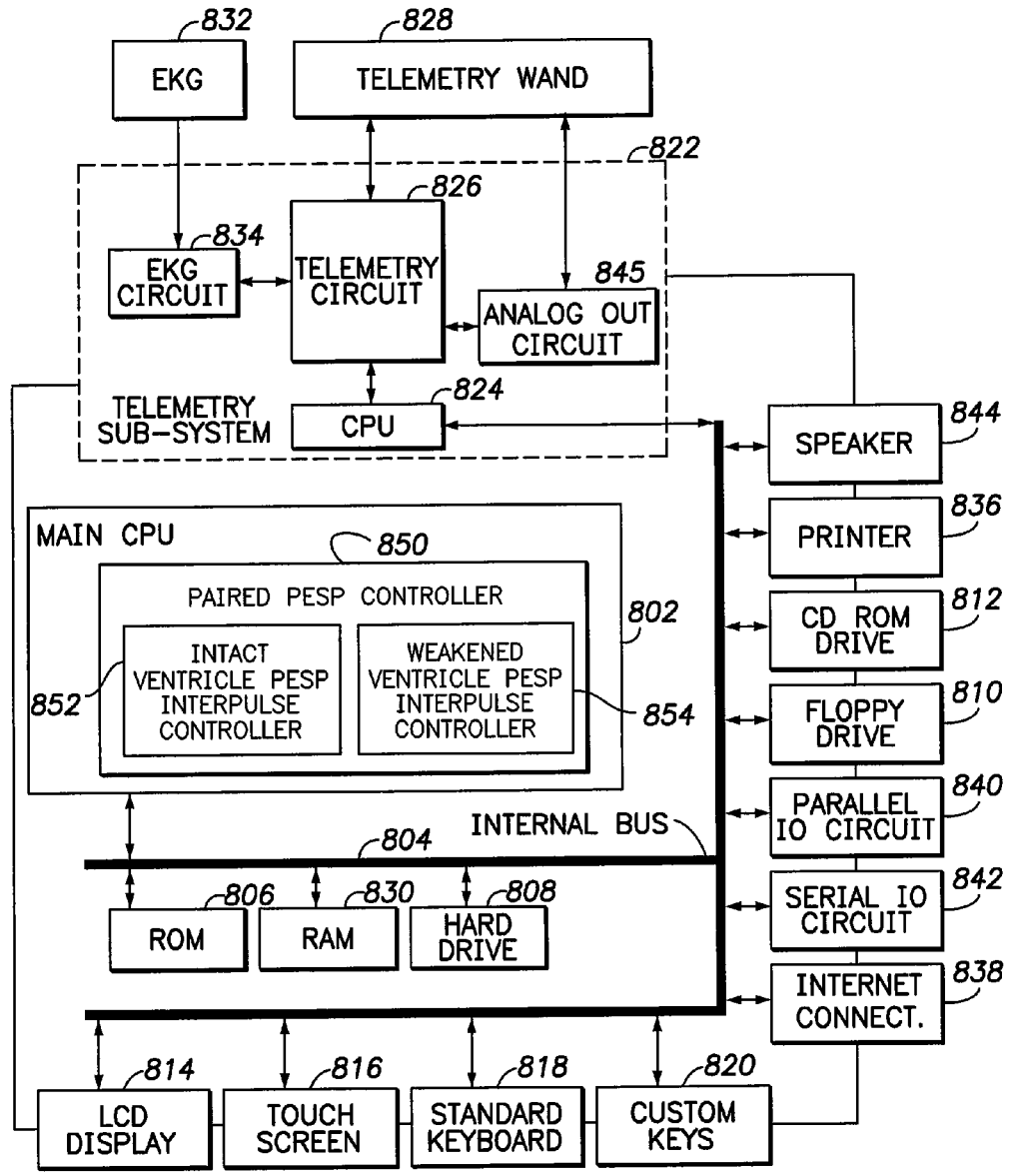
FIG. 13 is a functional block diagram illustrating components of the external device programmer of FIG. 3 and particularly illustrating programmer-based components for performing or controlling the techniques of FIGS. 4-10.

FIG. 13 illustrates pertinent components of an external programmer 16 for use in programming the device of FIG. 12 and for performing or controlling the above-described PESP techniques. For the sake of completeness, other device programming functions are also described herein. Generally, the programmer permits a physician, clinician or other user to program the operation of the implanted device and to retrieve and display information received from the implanted device such as intracardiac electrogram (IEGM) data and device diagnostic data. Additionally, the external programmer can be optionally equipped to receive and display electrocardiogram (ECG) data from separate external surface ECG leads that may be attached to the patient. Depending upon the specific programming of the external programmer, programmer 16 may also be capable of processing and analyzing data received from the implanted device and from the ECG leads to, for example, render preliminary diagnosis as to medical conditions of the patient or to the operations of the implanted device.

Now, considering the components of programmer 108, operations of the programmer are controlled by a CPU 802, which may be a generally programmable microprocessor or microcontroller or may be a dedicated processing device such as an ASIC or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency WI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 108 to retrieve data stored within any implanted devices and to also retrieve ECG data from ECG leads, if any, coupled to the patient. To this end, CPU 802 transmits appropriate signals to a telemetry subsystem 822, which provides components for directly interfacing with the implanted devices, and the ECG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an ECG circuit 834 for receiving surface ECG signals from a surface ECG system 832. In other implementations, the ECG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the device also includes the data stored within the recalibration database of the device (assuming the device is equipped to store that data.) Data retrieved from the implanted devices is stored by external programmer 108 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 108, the implanted devices may be further controlled to transmit additional data in real time as it is detected by the implanted devices, such as additional IEGM data, lead impedance data, and the like. Additionally, or in the alternative, telemetry subsystem 822 receives ECG signals from ECG leads 832 via an ECG processing circuit 834. As with data retrieved from the implanted device itself, signals received from the ECG leads are stored within one or more of the storage devices of the external programmer. Typically, ECG leads output analog electrical signals representative of the ECG. Accordingly, ECG circuit 834 includes analog to digital conversion circuitry for converting the signals to digital data appropriate for further processing within the programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted devices and from optional external ECG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the ECG leads, including displays of ECGs, IEGMs, and statistical patient information. Any or all of the information displayed by programmer may also be printed using a printer 836.

Additionally, CPU 802 also includes a paired PESP controller 850 that includes an intact ventricle PESP interpulse controller 852 operative to determine the first interpulse interval for use with paired PESP pacing of the intact ventricle sufficient to achieve little or no potentiation. Controller 8550 also includes a weakened ventricle PESP interpulse controller 854 operative to determine the second interpulse interval for use with paired PESP pacing of the weakened ventricle sufficient to maximize potentiation. These values are transmitted to the implantable device for use therein to deliver paired PESP pacing to the intact ventricle using the first interpulse interval while delivering paired PESP to the weakened ventricle using the second interpulse interval to reduce contractility disequilibrium within the heart caused by the weakened ventricle. Although not specifically shown, CPU 802 can additionally include a potentiation maximizing system for determining interpulse intervals needed to maximize potentiation for use in the weakened ventricle and a potentiation minimizing system for determining interpulse intervals needed to minimize potentiation for use in the intact ventricle, as well as other components corresponding to components of the on-board PESP controller of FIG. 12.

Depending upon the implementation, the various components of the CPU may be implemented as separate software modules or the modules may be combined to permit a single module to perform multiple functions. In addition, although shown as being components of the CPU, some or all of these components may be implemented separately using ASICs or the like.

Programmer/monitor 108 also includes an internet connection 838 to permit direct transmission of data to other programmers via the public switched telephone network (PSTN) or other interconnection line, such as a T1 line or fiber optic cable or wireless connection (WiFi). Depending upon the implementation, the internet connection may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (I/O) ports might be provided, including USB ports, etc. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an ECG machine or chart recorder.

With the programmer configured as shown, a clinician or other user operating the external programmer is capable of retrieving, processing and displaying a wide range of information received from the implanted device and to reprogram the implanted device if needed. The descriptions provided herein with respect to FIG. 13 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable cardiac stimulation device equipped to deliver paired post-extrasystolic (PESP) pacing within a patient having an intact ventricle and a weakened ventricle, the method comprising:
   determining a first interpulse interval for use with paired PESP pacing of the intact ventricle sufficient to achieve only relatively minimal potentiation within the intact ventricle;
   determining a second interpulse interval for use with paired PESP pacing of the weakened ventricle sufficient to achieve relatively more significant potentiation within the weakened ventricle, wherein the determining comprises delivering test pulses at varying intervals, assessing the degree of potentiation achieved with each interval, and selecting the interval corresponding to a maximum potentiation; and
   delivering paired PESP pacing to the intact ventricle using the first interpulse interval while delivering paired PESP to the weakened ventricle using the second interpulse interval to reduce contractility disequilibrium within the heart caused by the weakened ventricle.

2. The method of claim 1 for use with a patient having a weakened right ventricle (RV) and a relatively intact left ventricle (LV) and wherein the first interpulse interval is an RV interpulse interval and second interpulse interval is an LV interpulse interval.

3. The method of claim 2 wherein the LV interpulse interval is set substantially shorter than the RV interpulse interval to provide relatively minimal extrasystolic potentiation within the LV and relatively more significant extrasystolic potentiation within the RV.

4. The method of claim 3 wherein the LV interpulse interval is set to provide substantially no potentiation within the LV.

5. The method of claim 3 wherein the RV interpulse interval is set to provide maximum potentiation within the RV.

6. The method of claim 1 for use with a patient having a weakened LV and a relatively intact RV and wherein the first interpulse interval is an LV interpulse interval and second interpulse interval is an RV interpulse interval.

7. The method of claim 6 wherein the RV interpulse interval is set substantially shorter than the LV interpulse interval to provide relatively minimal extrasystolic potentiation within the RV and relatively more significant extrasystolic potentiation within the LV.

8. The method of claim 6 wherein the RV interpulse interval is set to provide substantially no potentiation within the RV.

9. The method of claim 6 wherein the LV interpulse interval is set to provide maximum potentiation within the LV.

10. The method of claim 1 wherein the first and second interpulse intervals are set to substantially match contractilities of the left and right ventricles during continuous PESP paired pacing.

11. The method of claim 1 wherein the first and second interpulse intervals are input from an external system.

12. The method of claim 1 wherein the first and second interpulse intervals are set by the implantable system.

13. The method of claim 12 wherein the implantable system has at least one hemodynamic sensor providing hemodynamic signals representative of a contractility disequilibrium between the left and right ventricles and wherein the first and second interpulse intervals are set based on the hemodynamic signals to reduce contractility disequilibrium within the heart.

14. The method of claim 13 wherein the hemodynamic sensor is a left atrial pressure (LAP) providing LAP signals and wherein the first and second interpulse intervals are set based on the LAP signals to reduce LAP.

15. The method of claim 14 wherein implantable device is also equipped to adjust atrioventricular (AV/PV) and interventricular (VV) delays intervals and wherein one or both of the AV/PV and VV intervals are adjusted based on the LAP signals.

16. The method of claim 1 wherein the implantable device is also equipped to adjust a paired pacing rate and wherein the first and second interpulse intervals are adjusted in part based on the paired pacing rate.

17. A system for use with an implantable cardiac stimulation device equipped to deliver paired post-extrasystolic (PESP) pacing within a patient having an intact ventricle and a weakened ventricle, the system comprising:

an intact ventricle PESP interpulse controller operative to determine a first interpulse interval for use with paired PESP pacing of the intact ventricle sufficient to achieve only relatively minimal potentiation;

a weakened ventricle PESP interpulse controller operative to determine a second interpulse interval for use with paired PESP pacing of the weakened ventricle sufficient to achieve relatively more significant potentiation, wherein the controller is adapted to deliver test pulses at varying intervals, assess the degree of potentiation for each interval, and select the interval corresponding to a maximum potentiation; and a PESP interpulse contractility disequilibrium controller operative to deliver paired PESP pacing to the intact ventricle using the first interpulse interval while delivering paired PESP to the weakened ventricle using the second interpulse interval to reduce contractility disequilibrium within the heart caused by the weakened ventricle.

18. A system for use with an implantable cardiac stimulation device equipped to deliver paired post-extrasystolic (PESP) pacing within a patient having an intact ventricle and a weakened ventricle, the system comprising:

means for determining a first interpulse interval for use with paired PESP pacing of the intact ventricle sufficient to achieve only relatively minimal potentiation;

means for determining a second interpulse interval for use with paired PESP pacing of the weakened ventricle sufficient to achieve relatively more significant potentiation, wherein the means for determining the second interpulse interval comprises means for delivering test pulses at varying intervals, assessing the degree of potentiation for each interval, and selecting the interval corresponding to a maximum potentiation; and means for delivering paired PESP pacing to the intact ventricle using the first interpulse interval while delivering paired PESP to the weakened ventricle using the second interpulse interval to reduce contractility disequilibrium within the heart caused by the weakened ventricle.

* * * * *